United States Patent
Wu et al.

(10) Patent No.: US 10,568,551 B2
(45) Date of Patent: Feb. 25, 2020

(54) HEARING DIAGNOSIS DEVICE AND HEARING DIAGNOSIS METHOD

(71) Applicant: National Tsing Hua University, Hsinchu (TW)

(72) Inventors: Hau-Tieng Wu, Kaohsiung (TW); Pa-Chun Wang, Taipei (TW); Yi-Wen Liu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 114 days.

(21) Appl. No.: 15/716,520

(22) Filed: Sep. 27, 2017

(65) Prior Publication Data

US 2018/0368741 A1    Dec. 27, 2018

(30) Foreign Application Priority Data

Jun. 22, 2017    (TW) .............................. 106120866 A (51) Int. Cl.
*A61B 5/00*    (2006.01)
*A61B 5/12*    (2006.01)
(Continued)

(52) U.S. Cl.
CPC .............. *A61B 5/121* (2013.01); *A61B 5/125* (2013.01); *A61B 5/7275* (2013.01);
(Continued)

(58) Field of Classification Search
CPC ..... A61B 5/121; A61B 5/6817; A61B 5/0484; A61B 5/04845; G16H 80/00; H04R 25/30;
(Continued)

(56) References Cited

U.S. PATENT DOCUMENTS

2004/0267321 A1*  12/2004  Boileau .............. A61B 5/04525
                                                                    607/3
2005/0018858 A1*  1/2005  John ...................... A61B 5/121
                                                                    381/60
(Continued)

FOREIGN PATENT DOCUMENTS

CN    103845061    6/2014
CN    104545940    4/2015
(Continued)

OTHER PUBLICATIONS

Liu, Y.-W. et al., "Quasilinear reflection as a possible mechanism for suppressor-induced otoacoustic emission," J. Acoust. Soc. Am., 140 (6), Dec. 2016, pp. 4193-4203.

(Continued)

*Primary Examiner* — Navin Natnithithadha
*Assistant Examiner* — Andrey Shostak
(74) *Attorney, Agent, or Firm* — JCIPRNET (57) ABSTRACT

A hearing diagnosis device and a hearing diagnosis method are provided. The device includes a storage unit, an otoacoustic emission detecting module, and a hearing diagnosis management module. The storage unit stores a hearing diagnosis image sample database and a hearing information sample database. The otoacoustic emission detecting module is configured to perform an otoacoustic emission detecting operation by playing a test audio to an ear of a user to obtain a first hearing diagnosis image corresponding to the ear. The hearing diagnosis management module is configured to perform a hearing diagnosis operation according to the first hearing diagnosis image, a plurality of hearing diagnosis image samples of the hearing diagnosis image sample database, and a plurality of hearing information samples, respectively corresponding to the hearing diagnosis image samples, of the hearing information sample database, so as to determine first hearing information of the ear.

16 Claims, 7 Drawing Sheets

(51) Int. Cl.
H04R 25/00 (2006.01)
A61N 1/05 (2006.01)
G16H 30/40 (2018.01)
G16H 50/50 (2018.01)
G16H 50/70 (2018.01)
G16H 50/20 (2018.01)
A61M 5/172 (2006.01)
A61B 5/0484 (2006.01)

(52) U.S. Cl.
CPC .......... *A61N 1/0541* (2013.01); *G16H 30/40* (2018.01); *G16H 50/20* (2018.01); *G16H 50/50* (2018.01); *G16H 50/70* (2018.01); *H04R 25/30* (2013.01); *A61B 5/0484* (2013.01); *A61B 5/04845* (2013.01); *A61B 5/6817* (2013.01); *A61B 5/6867* (2013.01); *A61B 5/726* (2013.01); *A61B 5/7257* (2013.01); *A61B 2503/08* (2013.01); *A61B 2562/0204* (2013.01); *A61M 5/1723* (2013.01); *A61M 2210/0662* (2013.01)

(58) Field of Classification Search
CPC ........ A61N 1/0541; A61M 2210/0662; A61M 5/1723
See application file for complete search history.

(56) References Cited

U.S. PATENT DOCUMENTS

| 2007/0156063 | A1* | 7/2007 | Zoth | A61B 5/121 |
| | | | | 600/559 |
| 2012/0197153 | A1* | 8/2012 | Kraus | A61B 5/04845 |
| | | | | 600/545 |
| 2013/0182855 | A1* | 7/2013 | Choi | H04R 25/30 |
| | | | | 381/23.1 |
| 2015/0289787 | A1 | 10/2015 | Buchman et al. | |
| 2017/0332977 | A1* | 11/2017 | Dalhoff | A61B 5/7203 |
| 2019/0074076 | A1* | 3/2019 | Harma | G16H 20/00 |

FOREIGN PATENT DOCUMENTS

| TW | 374712 | 11/1999 |
| TW | 492264 | 6/2002 |
| TW | I372611 | 9/2012 |
| TW | I562763 | 12/2016 |

OTHER PUBLICATIONS

Tzu-Chi Liu et al., "Investigating the cochlear contribution to auditory pre-masking," Proc. Int. Congress on Acoustics, Buenos Aires, Argentina, Sep. 2016, pp. 1-9.

Yi-Wen Liu et al., "Close-loop simulation of the medial olivocochlear anti-masking effects," In Mechanics of Hearing: Protein to Perception, Karavitaki KD, Corey DP (eds). American Institute of Physics, Melville, Aug. 2014, pp. 1-5.

Yi-Wen Liu, "Stationary noise responses in a nonlinear model of cochlear mechanics: Iterative solutions in the frequency domain," J. Acoust. Soc. Am., 136(4), Oct. 2014, pp. 1788-1796.

Yi-Wen Liu, et al., "Suppression tuning of distortion-product otoacoustic emissions: Results from cochlear mechanics simulation," J. Acoust. Soc. Am., 133(2), Feb. 2013, pp. 951-961.

Yi-Wen Liu et al., "Distortion-product emissions from a cochlear model with nonlinear mechanoelectrical transduction in outer hair cells," J. Acoust. Soc. Am. vol. 127, Apr. 2010, pp. 2420-2432.

Yi-Wen Liu et al., "Outer hair cell electromechanical properties in a nonlinear piezoelectric model," J. Acoust. Soc. Am., vol. 126, No. 2, Aug. 2009, pp. 751-761.

"Office Action of Taiwan Counterpart Application", dated Apr. 30, 2018, p. 1-p. 3.

* cited by examiner

HEARING DIAGNOSIS DEVICE AND HEARING DIAGNOSIS METHOD

CROSS-REFERENCE TO RELATED APPLICATION

This application claims the priority benefit of Taiwan application serial no. 106120866, filed on Jun. 22, 2017. The entirety of the above-mentioned patent application is hereby incorporated by reference herein and made a part of this specification.

BACKGROUND OF THE INVENTION

Field of the Invention

The invention relates to a hearing diagnosis device and particularly relates to a hearing diagnosis device and a hearing diagnosis method.

Description of Related Art

Otoacoustic emission (OAE) is a conventional technique for testing the inner ear functionality. During the test, an earplug including an earphone and a microphone is placed in the ear canal of the subject under test. The outer hair cells in the cochlea will vibrate slightly with the sound played by the earphone, and a sound wave (vibrating sound) is generated simultaneously with the vibration. The microphone then receives this responsive sound wave, so as to draw an otoacoustic emission image according to the time and corresponding frequency and intensity (sound intensity) of the vibrating sound that the microphone receives from the outer hair cells. The drawn otoacoustic emission image may be used to evaluate the auditory system functionality of the subject under test.

According to the current technique, however, the otoacoustic emission image can only be used to determine whether the hearing of the subject passes or fails the test, and it cannot determine the current degree of hearing (or the degree of hearing impairment) of the subject, detect or determine the current physiological indexes of each part of the ear, or predict recovery of hearing of the subject under test.

SUMMARY OF THE INVENTION

The invention provides a hearing diagnosis device and a hearing diagnosis method for comparing an otoacoustic emission image of a subject under test with a plurality of samples in an otoacoustic emission image sample database to correspondingly determine a degree of hearing impairment of each part, so as to obtain hearing information of the subject under test.

In an embodiment of the invention, a hearing diagnosis device is provided. The device includes a storage unit, an otoacoustic emission detecting module, and a hearing diagnosis management module. The storage unit stores a hearing diagnosis image sample database and a hearing information sample database. The hearing diagnosis image sample database records a plurality of hearing diagnosis image samples. The hearing information sample database records a plurality of hearing information samples respectively corresponding to the hearing diagnosis image samples. The otoacoustic emission detecting module is configured to perform an otoacoustic emission detecting operation by playing a test audio to an ear of a user to obtain a first hearing diagnosis image corresponding to the ear. The hearing diagnosis management module is coupled to the storage unit and the otoacoustic emission detecting module and is configured to execute a hearing diagnosis operation corresponding to the first hearing diagnosis image according to the first hearing diagnosis image, the hearing diagnosis image samples, and the hearing information samples, so as to determine first hearing information of the ear.

In an embodiment of the invention, a hearing diagnosis method is provided. The method includes: performing an otoacoustic emission detecting operation by playing a test audio to an ear of a user to obtain a first hearing diagnosis image corresponding to the ear; and executing a hearing diagnosis operation corresponding to the first hearing diagnosis image according to the first hearing diagnosis image, a plurality of hearing diagnosis image samples, and a plurality of hearing information samples respectively corresponding to the hearing diagnosis image samples, so as to determine first hearing information of the ear.

Based on the above, the hearing diagnosis device and the hearing diagnosis method of the invention perform the otoacoustic emission detecting operation on the ear of the subject under test, so as to obtain the hearing diagnosis image. Then, through comparison between the hearing diagnosis image and the hearing diagnosis image sample database, the hearing information of the subject under test is determined correspondingly.

To make the aforementioned and other features and advantages of the invention more comprehensible, several embodiments accompanied with figures are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
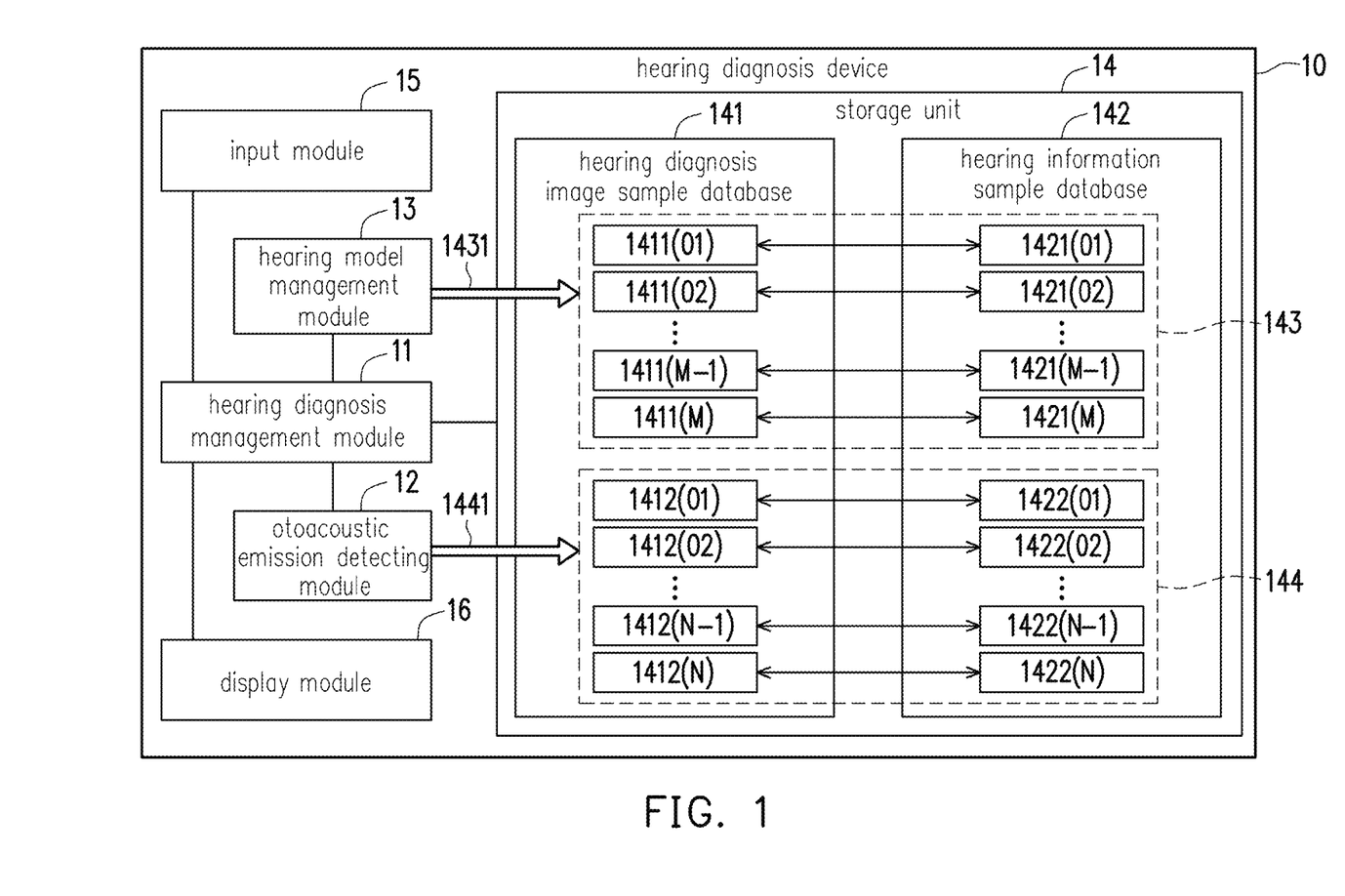
FIG. 1 is a block diagram of a hearing diagnosis device according to an embodiment of the invention.

FIG. 1 is a block diagram of a hearing diagnosis device according to an embodiment of the invention. Referring to FIG. 1, in this embodiment, a hearing diagnosis device 10 includes a hearing diagnosis management module 11, an otoacoustic emission detecting module 12, and a storage unit 14. The hearing diagnosis management module 11 is coupled to the otoacoustic emission detecting module 12 and the storage unit 14.

In an embodiment, the hearing diagnosis device 10 further includes a hearing model management module 13, which is coupled to the hearing diagnosis management module 11. In an embodiment, the hearing diagnosis device 10 further includes an input module 15 and a display module 16 coupled to the hearing diagnosis management module 11.

In this embodiment, the hearing diagnosis management module 11 is hardware with computing ability (e.g., a chipset, a processor, and so on) configured to control/access other components of the hearing diagnosis device 10, execute a hearing diagnosis operation, and control the overall operation of the hearing diagnosis device 10. In this embodiment, the hearing diagnosis management module 11 is a central processing unit (CPU), a microprocessor, other programmable processors, a digital signal processor (DSP), a programmable controller, an application specific integrated circuit (ASIC), a programmable logic device (PLD), or other similar devices, for example.

The otoacoustic emission detecting module 12 is (a specific hardware circuit or device) configured to execute an otoacoustic emission (OAE) detecting operation. More specifically, the otoacoustic emission detecting module 12 is configured to perform the otoacoustic emission detecting operation by playing a test audio to an ear of a user to obtain a first hearing diagnosis image corresponding to the ear. The otoacoustic emission detecting operation has the following two types: (1) transient evoked otoacoustic emissions (TEOAEs); and (2) distortion-product otoacoustic emissions (DPOAEs). Corresponding to different types of the otoacoustic emission detecting operations, the types of the test audio include: click, chirps, tone burst, frequency sweeps, pseudo-random noise, and so on, and different frequencies, (time) lengths, and intensities (e.g., sound pressure) may be set as required. The invention is not intended to limit the types and setting method of the test audio.

The input module 15 may be an input device in any form (or may be an external input device). The input device is, for example, a mouse, a keyboard, a scanner, a digital camera, a digital tablet, a microphone, a touchpad, a touch panel, and so on. The input module 15 allows the user (e.g., a subject under test, a test user, an examiner, and medical personnel) to input data or control the hearing diagnosis device via the input module 15.

The display module 16 is configured to display an image/content played by the hearing diagnosis device. The display module 16 is a liquid crystal display (LCD), a light-emitting diode (LED) display, a field emission display (FED), or other types of displays (screens), for example. The display module 16 may also be integrated with the input module 15 as a touch display module (e.g., a touch screen), composed of a resistive, capacitive, or optical touch panel, to provide both display and touch functions.

The storage unit 14 is a hard disk drive (HDD) in any form, a non-volatile memory storage device (e.g., a solid-state drive), or storage circuit units of other types, for example. In this embodiment, the storage unit 14 is configured to store a plurality of databases, which include a hearing diagnosis image sample database 141 and a hearing information sample database 142. The hearing diagnosis image sample database 141 records a plurality of hearing diagnosis image samples 1411(01) to 1411(M) and 1412(01) to 1412(N). M and N are positive integers. The hearing information sample database 142 records a plurality of hearing information samples 1421(01) to 1421(M) and 1422(01) to 1422(N) respectively corresponding to the hearing diagnosis image samples 1411(01) to 1411(M) and 1412(01) to 1412(N). For example, the hearing information sample 1421(01) corresponds to the hearing diagnosis image sample 1411(01). That is, hearing information recorded by the hearing information sample 1421(01) may include health information of the ear (also referred to as "tested ear") which is detected for generating the hearing diagnosis image sample 1411(01), identity information, and medical history information.

In this embodiment, health information of hearing information may include health information of each part of the tested ear of the corresponding hearing diagnosis image/hearing diagnosis image sample/soundprint image corresponding to the hearing information. For example, the health information may include degrees of hearing of different parts in the cochlea (e.g., functional indexes of outer hair cells at different parts), and physiological indexes related to different physiological structures, such as a plurality of physiological indexes of basilar membrane, reticular lamina, and/or outer hair cells of the organ of Corti, and so on (e.g., electric piezoelectric coefficient, cell membrane leakage conductivity, and cell membrane capacitance). In this embodiment, a hearing disease of the tested ear in the medical history information may be determined by the hearing diagnosis device according to the corresponding hearing diagnosis image of the hearing information to which the medical history information belongs.

In this embodiment, the identity information of the hearing information may include an identity of the tested ear of the corresponding hearing diagnosis image/hearing diagnosis image sample/soundprint image. For example, the identity information may include personal information (e.g., name, identification code, age and/or other physiological information) of a person (i.e., the subject under test) of the tested ear, and the tested ear may be determined as the left ear or right ear of the subject under test according to the identity information. In this embodiment, the health information may be determined by the hearing diagnosis management module 11 according to the corresponding hearing diagnosis image of the hearing information, to which the health information belongs.

In this embodiment, the medical history information of the hearing information may include a hearing disease history of the tested ear of the corresponding hearing diagnosis image sample/hearing diagnosis image sample/soundprint image (or further includes all or other health history of the person of the tested ear). The hearing disease history may record related information (e.g., course of the disease, symptom, and recovery information) of hearing diseases, such as Meniere's disease, sudden hearing loss, noise induced hearing loss, sensorineural hearing loss, age-related hearing loss, and so on, of the tested ear. In this embodiment, the hearing disease of the tested ear in the medical history information may be determined by the hearing diagnosis device according to the corresponding hearing diagnosis image of the hearing information, to which the medical history information belongs.

It should be noted that the user (e.g., the subject under test, the examiner, or the medical personnel) may also add information to the data stored in one or more databases via the input module 15. For example, the medical personnel may add an identity note related to the subject under test (tester, or test user) to the identity information of the hearing information corresponding to the subject under test. For example, the medical personnel may also input a diagnosis of the subject under test to the medical history information and the health information via the input module 15. It should be noted that the health information and the identity information may also be integrated into the medical history information.

In other words, through the hearing information, the user may learn diagnosis-related information of the ear corresponding to the hearing information.

It should be noted that, in order that the data stored in all the databases may be used for comparison and reference, the information stored in all the databases corresponds to the same test audio. For example, the test audio corresponding to the hearing diagnosis image sample 1411(01) (i.e., the hearing diagnosis image sample 1411(01) is generated by the test audio) is the same as the test audio corresponding to the hearing diagnosis image sample 1411(02).

In this embodiment, the hearing diagnosis image samples 1411(01) to 1411(M) and 1412(01) to 1412(N) may be divided into two groups, i.e., the hearing diagnosis image samples 1411(01) to 1411(M) of a simulation sample group 143 and the hearing diagnosis image samples 1412(01) to 1412(N) of a clinical sample group 144. Moreover, the hearing information samples 1421(01) to 1421(M) and 1422(01) to 1422(N) may also be divided into two groups, i.e., the hearing information samples 1421(01) to 1421(M) of the simulation sample group 143 and the hearing information samples 1422(01) to 1422(N) of the clinical sample group 144. A method of generating the hearing diagnosis image samples 1411(01) to 1411(M) and the hearing information samples 1421(01) to 1421(M) of the simulation sample group 143, and the hearing diagnosis image samples 1412(01) to 1412(N) and the hearing information samples 1422(01) to 1422(N) of the clinical sample group 144 is described hereinafter.

In this embodiment, the hearing model management module 13 is configured to respectively generate a plurality of hearing models according to a plurality of parameter sets, wherein each of the parameter sets includes a plurality of parameters corresponding to different parts of a human ear and a health function corresponding to the human ear.

More specifically, the hearing model is a cochlea biophysical model for describing reaction of the cochlea of human or other animal, for example, which may simplify wave propagation of the vibrating sound (echo/reverberation) of the cochlea (the vibrating sound is generated by the cochlea in response to the received test audio) into a transmission line and embed an electric model of the outer hair cells, so as to describe a positive feedback regarding to the wave propagation. In addition, the hearing model may also simulate the vibration and frequency response of each part of the basilar membrane of the cochlea caused by any sound, and the vibration and sound wave of TEOAEs and DPOAEs that the cochlea sends back through the middle ear to the outer ear.

Here, the parameters in one parameter set corresponding to one hearing model include first type parameter(s) and second type parameter(s). The first type parameters include material properties of the organ of Corti of each part of the cochlea (cochlea biophysical model) from high frequency to low frequency, e.g., stiffness coefficient and mass density of basilar membrane; stiffness coefficient and mass density of reticular lamina; and non-linear saturation relation, electromotility piezoelectric coefficient, cell membrane leakage conductivity, and cell membrane capacitance of the outer hair cells. The second type parameters include cross-sectional areas of each part of the cochlea.

The health function is a vibration-current transfer function $r(x)$ of the outer hair cells of the cochlea (cochlea biophysical model), which is directly related to the potentials of different parts of the cochlea ("x" indicates different positions of the cochlea from the base to the apex). In other words, if "x" that indicates the "x" position of the cochlea is inputted to the health function $r(x)$, a degree of hearing Y ($r(x)=Y$) of the "x" position of the cochlea is obtained (outputted trough the health function). If the degree of hearing Y=0, it indicates that the electrical potential of the "x" position of the cochlea is completely insufficient and the outer hair cells are completely non-functional or the hearing is completely lost. If the degree of hearing Y=1, it indicates that the potential of the "x" position is sufficient and the outer hair cells are fully functional or the hearing is not having any loss. The degree of hearing Y may be any value between 0 and 1.

After the parameters and health functions of different parameter sets are set, the hearing model management module 13 generates the hearing models according to the parameter sets.

In this embodiment, the hearing model management module 13 respectively inputs the test audio to the generated hearing models to generate (draw) a plurality of hearing diagnosis images (also referred to as "second hearing diagnosis images") respectively corresponding to the parameter sets of the hearing models, and the hearing model management module 13 uses the parameter sets to generate a plurality of pieces of second hearing information respectively corresponding to the second hearing diagnosis images. More specifically, because the parameters and health functions of the parameter sets may be used to describe the physiological parameters and degrees of hearing of different parts of the cochlea, the hearing model management module 13 may generate health information corresponding to the hearing models according to the parameters and health functions of the parameter sets. In other words, the hearing model generated according to one parameter set may respond to the inputted test audio to simulate the vibrating sound of the outer hair cells (corresponding to the hearing model) in response to the test audio, and output the hearing diagnosis image correspondingly. The (outputted) hearing diagnosis image may then be used to describe the vibrating sound/otoacoustic emission reflected by the ear that matches the physiological characteristics of the parameter set, and the hearing information (health information) correspondingly generated by the parameter set may describe the health condition of each part of the cochlea of the ear that matches the physiological characteristics of the parameter set. For example, the parameter corresponding to the basilar membrane may be used to describe the elasticity of the basilar membrane; and the health function corresponding to the outer hair cells may be used to describe the integrity of the function of the outer hair cells (magnification of bioelectric energy), e.g., 0% to 100% (100% indicates healthy outer hair cells).

In other words, by setting a large number of parameter sets, a large number of hearing models may be generated for rapidly and quantitatively simulating otoacoustic emissions generated by ears with different physiological characteristics/health conditions. Accordingly, it may solve the problem that it is difficult to clinically obtain plenty results (hearing diagnosis images) of performing otoacoustic emission detecting operations in a short period of time.

In this embodiment, the hearing model management module 13 takes (uses) the generated second hearing diagnosis images as the hearing diagnosis image samples 1411(01) to 1411(M) (also referred to as "second hearing diagnosis image samples") divided into the simulation sample group 143, and stores the second hearing diagnosis image samples to the hearing diagnosis image sample database 141, wherein the hearing model management module takes (uses) the second hearing information as the hearing information samples 1421(01) to 1421(M) (also referred to as "second hearing information samples"), respectively corresponding to the second hearing diagnosis image samples, divided into the simulation sample group 143, and stores the second hearing information samples to the hearing information sample database 142.

Regarding the clinical sample group 144, in this embodiment, in response to completion of determining the first hearing information of the ear, the hearing diagnosis management module stores the first hearing diagnosis image as a third hearing diagnosis image sample to the clinical sample group 144, and stores the determined first hearing information as a corresponding third hearing information sample to the clinical sample group 144. More specifically, if the hearing diagnosis management module 11 determines (clinically) the first hearing information of the tested ear according to the first hearing diagnosis image measured and generated by the otoacoustic emission detecting module, and the hearing diagnosis management module 11 further uses the determined first hearing information and the corresponding first hearing diagnosis image as samples and respectively stores them to the hearing information sample database and the hearing diagnosis image sample database divided into the clinical sample group 144.

Briefly, the hearing diagnosis image samples and the hearing information samples of the simulation sample group 143 may be regarded as being obtained via the hearing model management module 13 (as indicated by the arrow 1431, for example), and the hearing diagnosis image samples and the hearing information samples of the clinical sample group 144 may be regarded as being obtained via the otoacoustic emission detecting module 12 (as indicated by the arrow 1441, for example).

It should be noted that the hearing diagnosis image samples 1412(01) to 1412(N) and the corresponding hearing information 1422(01) to 1422(N) in the clinical sample group may also include the determined hearing information corresponding to the hearing diagnosis images obtained by the otoacoustic emission detecting operation and/or hearing diagnosis operation performed by other hearing diagnosis devices. Moreover, in another embodiment, the health information of the ear of a subject under test may be diagnosed first by other methods, and then be combined with the identity information and medical history information of the subject under test to serve as the hearing information of the ear. Thereafter, the otoacoustic emission detecting operation is performed on the ear of the subject under test to obtain a hearing diagnosis image. At last, the hearing information and the hearing diagnosis image are respectively used as the hearing information sample and the hearing diagnosis image sample divided into the clinical sample group and respectively stored to the hearing information sample database and the hearing diagnosis image sample database.

Figure 2:
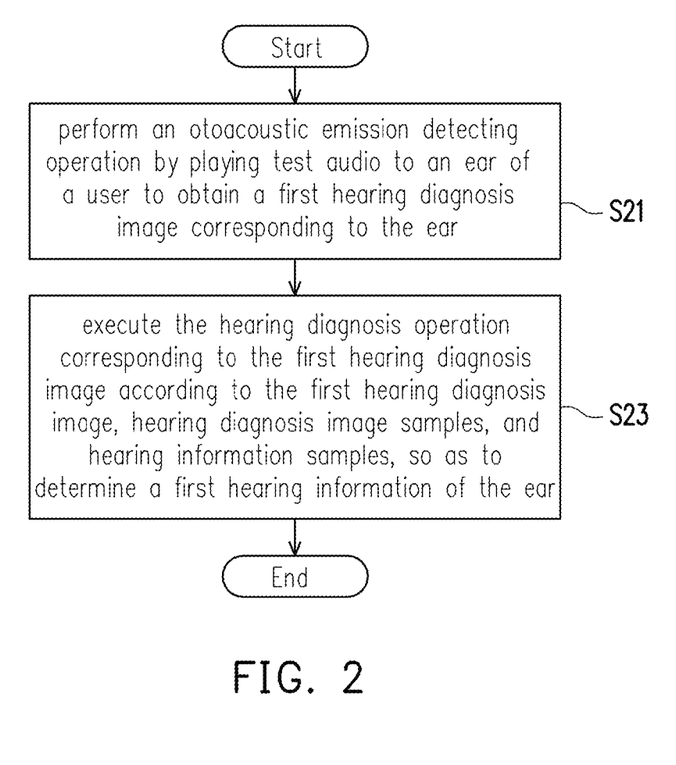
FIG. 2 is a flowchart of a hearing diagnosis method according to an embodiment of the invention.

FIG. 2 is a flowchart of a hearing diagnosis method according to an embodiment of the invention. Referring to FIG. 2, in Step S21, the otoacoustic emission detecting module 12 performs an otoacoustic emission detecting operation by playing test audio to an ear (the tested ear) of a user (the subject under test) to obtain a first hearing diagnosis image corresponding to the ear. More specifically, the otoacoustic emission detecting operation is usually performed to detect the condition of the cochlea, so as to evaluate whether the inner ear is abnormal. The cochlea is an auditory organ in the inner ear, which receives the test audio being played, and at the same time, generates a low-intensity echo sound (also called a vibrating sound) by movement of the outer hair cells inside and transmits the vibrating sound outward through the middle ear and the outer ear from the cochlea. This effect is called otoacoustic emission. The otoacoustic emission detecting module 12 is coupled to a sound receiving device (e.g., a probe microphone) and a sound source device (e.g., an earphone or a speaker). When the otoacoustic emission detecting operation is executed, the sound receiving device is placed in the ear of the user (also referred to as "subject under test"), and the test audio is sent to the ear of the subject under test by the sound source device. The probe microphone is used to receive the vibrating sounds generated correspondingly by the outer hair cells of different parts of the cochlea in response to the received test audio. The otoacoustic emission detecting module 12 draws an otoacoustic emission waveform, i.e., hearing diagnosis image (e.g., the first hearing diagnosis image), according to sound intensities (the unit is sound pressure, for example) of the vibrating sounds received sequentially.

Figure 5A:
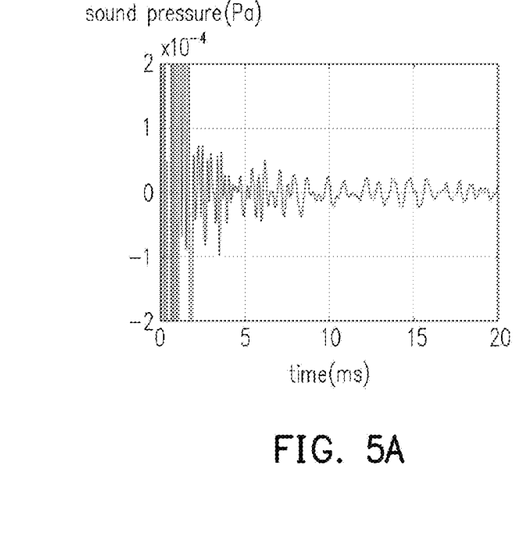
FIG. 5A is a hearing diagnosis image with an otoacoustic emission waveform according to an embodiment of the invention.

FIG. 5A is a hearing diagnosis image with an otoacoustic emission waveform according to an embodiment of the invention. Referring to FIG. 5A, for example, the hearing diagnosis image records the otoacoustic emission waveform obtained by performing the otoacoustic emission detecting operation on the ear of the subject under test, and the sound pressure of the otoacoustic emission waveform fluctuates with time. That is, the horizontal axis coordinate of the otoacoustic emission waveform represents the time when the vibrating sound is received (the unit is ms, for example) and the vertical axis coordinate represents the value of the sound pressure (the unit is Pa, for example) of the vibrating sound that is received. In other words, the otoacoustic emission waveform of the hearing diagnosis image may be used to represent the sound pressures of the vibrating sounds (also referred to as "responsive vibrating sound" or "echo") that the ear (cochlea) generates with time in response to the test audio played to the ear. Nevertheless, it should be noted that the invention is not limited thereto. In another embodiment, for example, the otoacoustic emission waveform of the hearing diagnosis image may be drawn in other forms, or based on other different horizontal/vertical axis units.

Reverting to FIG. 2, after obtaining the first hearing diagnosis image, in Step S23, the hearing diagnosis management module 11 executes a hearing diagnosis operation corresponding to the first hearing diagnosis image according to the first hearing diagnosis image, hearing diagnosis image samples, and hearing information samples, so as to determine a first hearing information of the ear. Processes of the hearing diagnosis operation are described in detail hereinafter with reference to FIG. 3.

Figure 3:
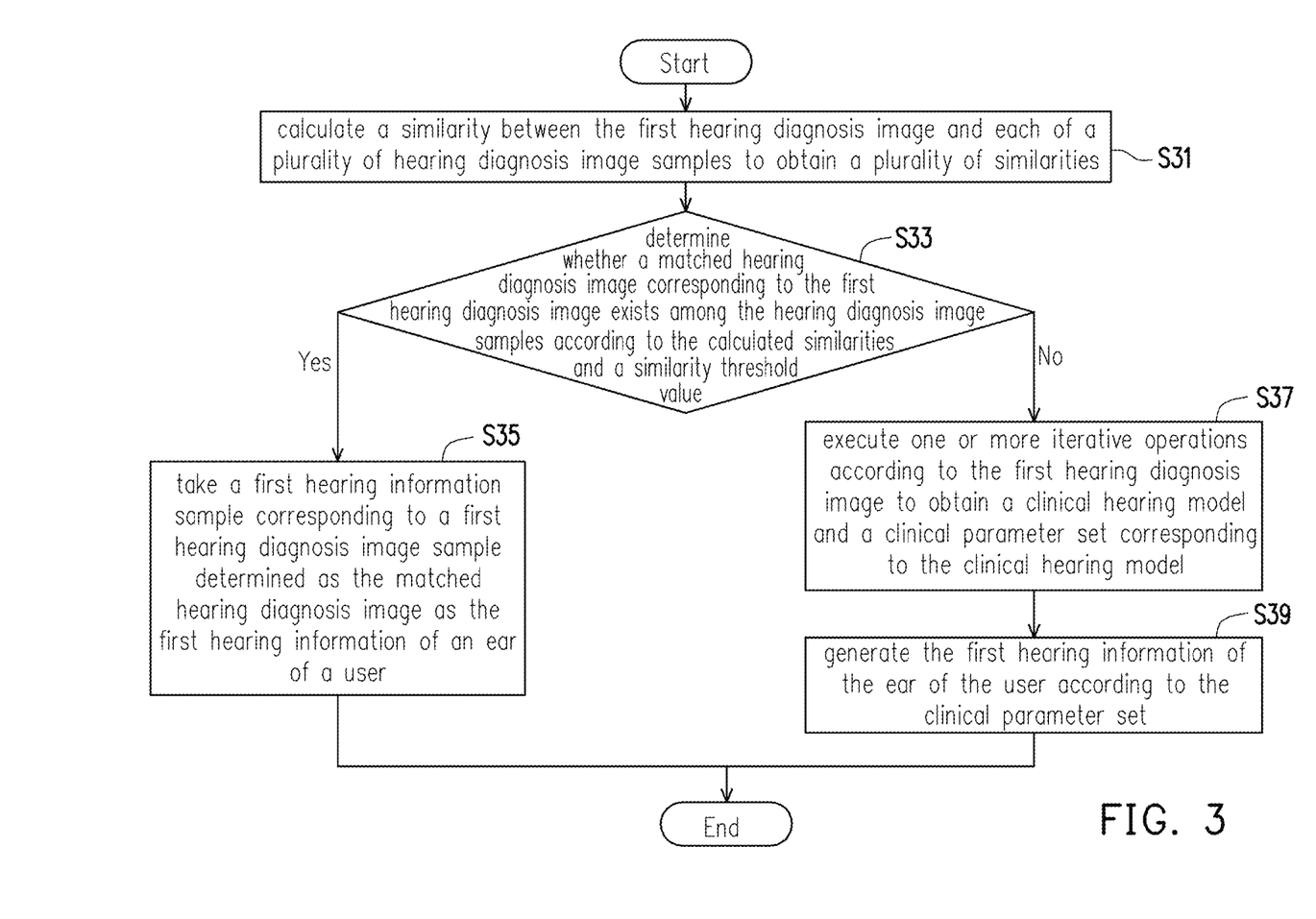
FIG. 3 is a flowchart of a hearing diagnosis operation according to an embodiment of the invention.

FIG. 3 is a flowchart of the hearing diagnosis operation according to an embodiment of the invention. Referring to FIG. 3, in Step S31, the hearing diagnosis management module 11 calculates a similarity between the first hearing diagnosis image and each of a plurality of hearing diagnosis image samples to obtain a plurality of similarities. More specifically, the hearing diagnosis management module 11 accesses the databases of the storage unit 14 (e.g., the hearing diagnosis image sample database 141 and the hearing information sample database 142) and reads a plurality of hearing diagnosis image samples therefrom. In this embodiment, the hearing diagnosis management module 11 performs an image comparison operation on the first hearing diagnosis image and the hearing diagnosis image samples one by one to calculate the similarity between each hearing diagnosis image sample and the first hearing diagnosis image (to obtain a plurality of similarities).

Then, in Step S33, the hearing diagnosis management module 11 determines whether a matched hearing diagnosis image corresponding to the first hearing diagnosis image exists among the hearing diagnosis image samples according to the calculated similarities and a similarity threshold value. More specifically, after calculating the similarities (also referred to as "similarity scores") between the hearing diagnosis image samples and each of the first hearing diagnosis image, the hearing diagnosis management module 11 determines whether a maximum similarity (also referred to as "first similarity") of the similarities exceeds the similarity threshold value. If the first similarity exceeds the similarity threshold value, the hearing diagnosis management module 11 determines that the first hearing diagnosis image sample corresponding to the first similarity is the matched hearing diagnosis image corresponding to the first hearing diagnosis image (that is, the first hearing diagnosis image sample is a sample that is reliable and similar to the first hearing diagnosis image). Then, the hearing diagnosis management module 11 proceeds to Step S35 and takes (uses) a first hearing information sample corresponding to a first hearing diagnosis image sample determined as the matched hearing diagnosis image as a first hearing information of an ear of a user. In other words, the hearing diagnosis management module 11 determines that the first hearing information sample corresponding to the first hearing diagnosis image sample may be used to describe the hearing condition of the tested ear of the subject under test. For example, the hearing diagnosis management module 11 uses the health information in the first hearing information sample as the health information (e.g., the degree of hearing of each part of the tested ear or the physiological index of each part of the tested ear) of the tested ear, and displays the health information of the tested ear via the display module 16. Accordingly, the subject under test may objectively learn the health condition of the subject's ear, and the medical personnel (e.g., doctor) may refer to the displayed health information for further diagnosis. In addition, for example, the hearing diagnosis management module 11 may further display the identity information and the medical history information recorded in the first hearing information sample to be provided to the subject under test, the medical personnel, or other users other available information related to the ear (i.e., the ear corresponding to the first hearing diagnosis image sample) similar to the tested ear.

If the first similarity does not exceed the similarity threshold value, the hearing diagnosis management module 11 determines that the hearing diagnosis image samples do not include the matched hearing diagnosis image corresponding to the first hearing diagnosis image, and the hearing diagnosis management module 11 does not take (use) any of the hearing information samples as the first hearing information of the tested ear, and the hearing diagnosis management module 11 uses other methods to determine the first hearing information. For example, the hearing diagnosis management module 11 tries to find a hearing model (also referred to as "clinical hearing model") that is most similar to the tested ear and determines the health information of the tested ear according to a plurality of parameter sets of the clinical hearing model. More specifically, referring to FIG. 3 again, in this embodiment, if the hearing diagnosis management module 11 determines that the hearing diagnosis image samples do not include the matched hearing diagnosis image corresponding to the first hearing diagnosis image, the hearing diagnosis management module 11 proceeds to Step S37 and executes one or more iterative operations according to the first hearing diagnosis image to obtain a clinical hearing model and a clinical parameter set corresponding to the clinical hearing model. Processes of the iterative operation are described in detail hereinafter with reference to FIG. 4.

Figure 4:
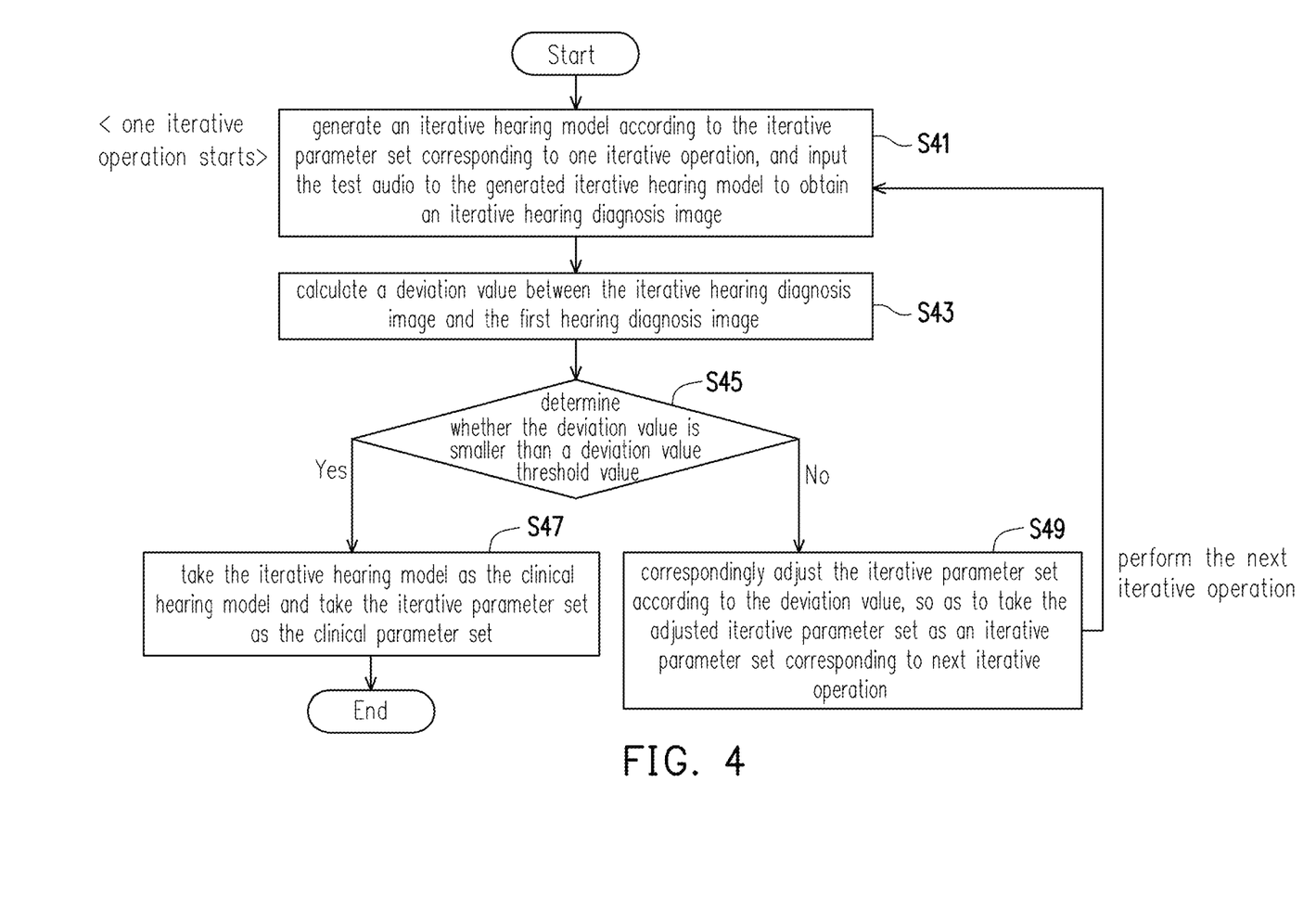
FIG. 4 is a flowchart of executing an iterative operation to obtain clinical parameter sets according to an embodiment of the invention.

FIG. 4 is a flowchart of executing the iterative operation to obtain the clinical parameter sets according to an embodiment of the invention. Referring to FIG. 4, one iterative operation starts. In Step S41, the hearing diagnosis management module 11 generates an iterative hearing model according to an iterative parameter set corresponding to one iterative operation, and inputs the test audio to the generated iterative hearing model to obtain an iterative hearing diagnosis image.

More specifically, the iterative parameter set is similar to the aforementioned parameter set in meaning, and the word "iterative" is used to describe that the parameter set is to be adjusted and updated with each of a plurality of executed iterative operations. The iterative parameter set (initial iterative parameter set) of the first iterative operation may be preset. Alternatively, the hearing diagnosis management module 11 may take (use) the parameter set of the hearing model corresponding to the hearing diagnosis image that is most similar to the first hearing diagnosis image in the simulation sample group 143 as the initial iterative parameter set. Then, as the method of generating the hearing model described above, the hearing diagnosis management module 11 generates the hearing model (also referred to as "iterative hearing model") according to the iterative parameter set, and inputs the test audio to the generated iterative hearing model to obtain an outputted hearing diagnosis image (also referred to as "iterative hearing diagnosis image").

Next, in Step S43, the hearing diagnosis management module 11 calculates a deviation value between the iterative hearing diagnosis image and a first hearing diagnosis image. More specifically, the hearing diagnosis management module 11 calculates the deviation value (also referred to as "error value") between the iterative hearing diagnosis image and the first hearing diagnosis image by image comparison or by calculating sound pressure differences between the iterative hearing diagnosis image and the first hearing diagnosis image at a plurality of times.

After calculating the deviation value, in Step S45, the hearing diagnosis management module 11 determines whether the deviation value is smaller than a deviation value threshold value. The deviation value threshold value is preset. If the deviation value is smaller than the deviation value threshold value, the hearing diagnosis management module 11 proceeds to Step S47 and takes (uses) the iterative hearing model as a clinical hearing model and uses the iterative parameter set as a clinical parameter set. In other words, if the difference between the iterative hearing diagnosis image obtained by using the current iterative parameter set and the first hearing diagnosis image is small to a certain level, the hearing diagnosis management module 11 determines that the iterative hearing model may be used to simulate the cochlea of the tested ear, and the parameters and health functions in the iterative parameter set may be used to describe the health status of the tested ear corresponding to the first hearing diagnosis image. In addition, the hearing diagnosis management module 11 uses the iterative hearing model as the clinical hearing model and uses the iterative parameter set as the clinical parameter set, and ends all the entire iterative operation(s) (i.e., would not perform the next iterative operation).

If the deviation value is not smaller than the deviation value threshold value, the hearing diagnosis management module 11 proceeds to Step S49 and correspondingly adjusts the iterative parameter set according to the deviation value, so as to take (use) the adjusted iterative parameter set as an iterative parameter set corresponding to next iterative operation. In other words, if the difference between the iterative hearing diagnosis image (obtained by using the current iterative parameter set) and the first hearing diagnosis image is not small to a certain level (value), the hearing diagnosis management module 11 determines that the parameters and health functions in the current used iterative parameter set cannot be used to describe the health state of the tested ear corresponding to the first hearing diagnosis image, and the hearing diagnosis management module 11 adjusts the parameters and health functions in the current used iterative parameter set (this round of iterative operation is ended) and re-executes Step S41 to take (use) the adjusted iterative parameter set to perform the next iterative operation (that is, in the next iterative operation, a new iterative hearing model is generated according to the adjusted iterative parameter set, and the test audio is inputted to the generated new iterative hearing model to obtain a new iterative hearing diagnosis image). Nevertheless, the invention is not intended to limit how the iterative parameter set is adjusted.

Reverting to FIG. 3, in Step S39, the hearing diagnosis management module 11 generates the first hearing information of the ear of the user according to the clinical parameter set. More specifically, as described above, after obtaining the clinical parameter set, the hearing diagnosis management module 11 determines that the parameters and health functions in the clinical parameter set may be used to describe the health information of the ear of the (tested) user corresponding to the first hearing diagnosis image and correspondingly directly uses the health information described according to the parameters and health functions in the clinical parameter set to generate the first hearing information. For example, the hearing diagnosis management module 11 combines the health information, the identity information and the medical history information of the ear of the user to generate the first hearing information.

Figure 5B:
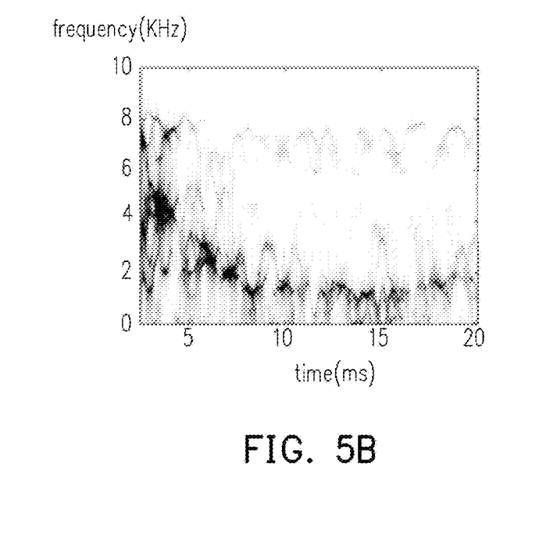
FIG. 5B is a soundprint image generated according to an otoacoustic emission waveform according to an embodiment of the invention.

FIG. 5B is a soundprint generated according to an otoacoustic emission waveform according to an embodiment of the invention. Referring to FIG. 5A and FIG. 5B, in this embodiment, the otoacoustic emission detecting module 12 is further configured to generate a first soundprint image (as shown in FIG. 5B) according to the otoacoustic emission waveform (as shown in FIG. 5A) of the first hearing diagnosis image, and store the first soundprint image to a first soundprint image history record, wherein the horizontal axis coordinate of the first soundprint image represents time and the vertical axis coordinate of the first soundprint image represents frequency. More specifically, the otoacoustic emission detecting module 12 converts the otoacoustic emission waveform to a concentration image (also referred to as "soundprint image") by a time-frequency analysis method of ConceFT (concentration in frequency and time). The ConceFT time-frequency analysis method is a type of non-linear conversion, which utilizes in a re-assignment ways to focus the result of the traditional Fourier or wavelet transform on an instantaneous frequency of the signal at each time and uses a random windowing function to obtain the average, so as to further enhances the clarity of the generated soundprint image. Moreover, the otoacoustic emission detecting module 12 stores the obtained (converted) soundprint image to the corresponding soundprint image history record.

Figure 6:
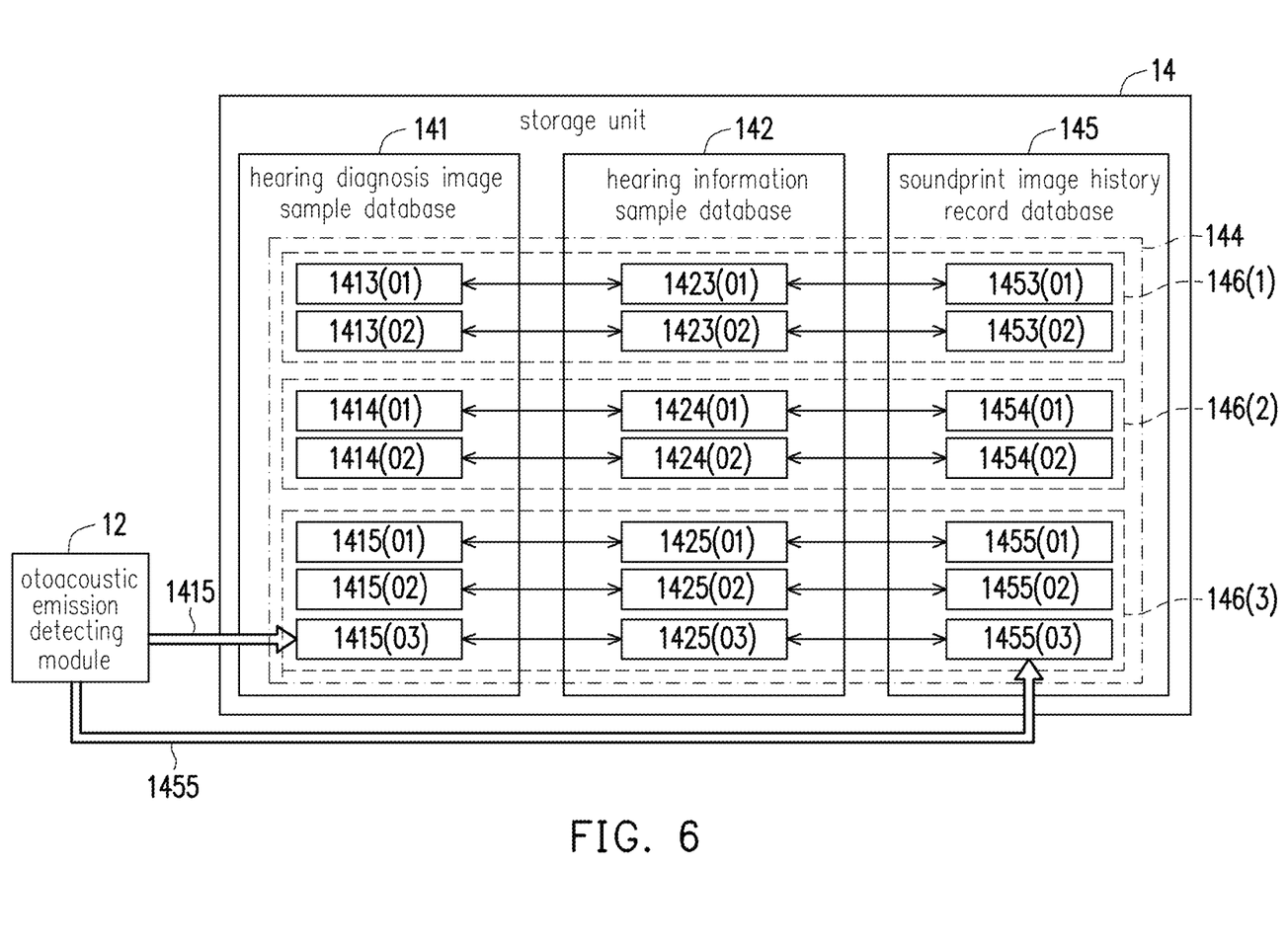
FIG. 6 is a block diagram of a plurality of databases according to an embodiment of the invention.

FIG. 6 is a block diagram of a plurality of databases according to an embodiment of the invention. Referring to FIG. 6, in this embodiment, the databases stored in the storage unit 14 include the hearing diagnosis image sample database 141, the hearing information sample database 142, and a soundprint image history record database 145. The hearing diagnosis image sample database 141 and the hearing information sample database 142 have been described above and thus are not repeated hereinafter. The soundprint image history record database 145 is configured to record a plurality of soundprint image history records.

For example, it is assumed that, in the clinical sample group, the hearing diagnosis image sample database 141 originally includes the hearing diagnosis image samples 1413(01), 1413(02), 1414(01), 1414(02), and 1415(01) to 1415(02); the hearing information sample database 142 originally includes the hearing information samples 1423 (01), 1423(02), 1424(01), 1424(02), and 1425(01) to 1425 (02); and the soundprint image history record database 145 originally includes soundprint images 1453(01), 1453(02), 1454(01), 1454(02), and 1455(01) to 1455(02). The soundprint images 1453(01) and 1453(02) corresponding to a tested ear 146(1) respectively correspond to the hearing diagnosis image samples 1413(01) and 1413(02) of the tested ear 146(1), and respectively correspond to the hearing information samples 1423(01) and 1423(02) of the tested ear 146(1); the soundprint images 1454(01) and 1454(02) corresponding to a tested ear 146(2) respectively correspond to the hearing diagnosis image samples 1414(01) and 1414(02) of the tested ear 146(2), and respectively correspond to the hearing information samples 1424(01) and 1424(02) of the tested ear 146(2); and the soundprint images 1455(01) and 1455(02) corresponding to a tested ear 146(3) respectively correspond to the hearing diagnosis image samples 1415(01) and 1415(02) of the tested ear 146(3), and respectively correspond to the hearing information samples 1455(01) and 1455(02) of the tested ear 146(3). If the otoacoustic emission detecting module 12 performs the otoacoustic emission detecting operation on the ear of the user (e.g., the tested ear 146(3)) and correspondingly obtains the first hearing diagnosis image, the otoacoustic emission detecting module 12 converts the first hearing diagnosis image to the first soundprint image 1455(03) and stores it to the first soundprint image history record that has included a plurality of first soundprint images 1455(01) to 1455(02) (as indicated by the arrow 1455) of the tested ear 146(3), and uses the first hearing diagnosis image as a third hearing diagnosis image 1415(03) and stores it to the hearing diagnosis image sample database 141 (as indicated by the arrow 1415). The first soundprint images 1455(01) to 1455(03) recorded in the first soundprint image history record are soundprint images obtained by performing the otoacoustic emission detecting operation at different time points. For example, the first soundprint images 1455(01) to 1455(03) may be arranged in a chronological order. That is, the first soundprint image 1455(01) is the earliest (oldest) first soundprint image corresponding to the tested ear 146(3) and the first soundprint image 1455(03) is the latest (most new) first soundprint image corresponding to the tested ear 146(3).

In this embodiment, after converting the first hearing diagnosis image to the first soundprint image 1455(03), the hearing diagnosis management module 11 analyzes the first soundprint images 1455(01) to 1455(03) corresponding to different time points in the first soundprint image history record to determine first hearing recovery information of the ear 146(3) of the user, wherein the first hearing recovery information includes a recovery prediction, a recovery progress, a recovery probability of the hearing of the ear, or a combination thereof. The recovery prediction indicates the percentage of health condition that the ear is expected to recover in the future, and may predict the time required for the recovery. The recovery progress indicates whether the ear is currently gradually recovering (whether the degree of hearing of the ear is improving) and whether the recovery is good. The recovery probability indicates whether it is possible for the ear to recover and the probability of the recovery.

More specifically, the hearing diagnosis management module 11 calculates a plurality of first soundprint densities respectively corresponding to the first soundprint images according to images of a specific region of the first soundprint images, wherein the hearing diagnosis management module 11 determines the first hearing recovery information according to variation of the first soundprint densities and adds the determined first hearing recovery information to the first hearing information (e.g., the health information or medical history information of the first hearing information). A horizontal axis range (time range) of the specific region may be set to 1-20 ms while a vertical axis range (frequency range) of the specific region may be set to 1-10 kHz. The following is described with reference to FIG. 7A to 7C.

Figure 7A:
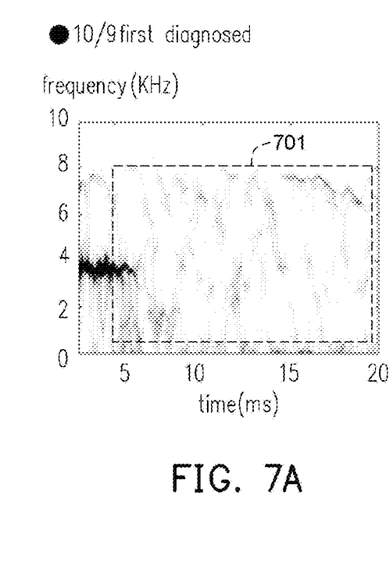
FIG. 7A, FIG. 7B, and FIG. 7C are soundprint images at different time points according to an embodiment of the invention.
Figure 7B:
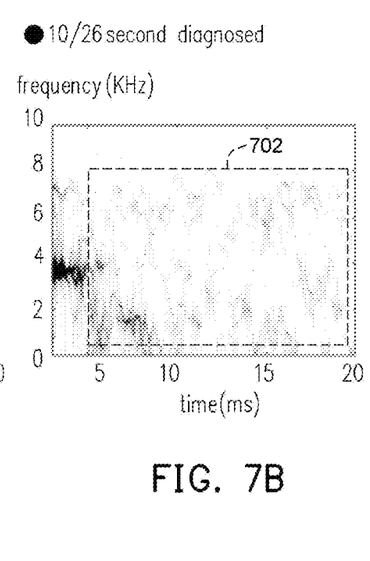
Figure 7C:
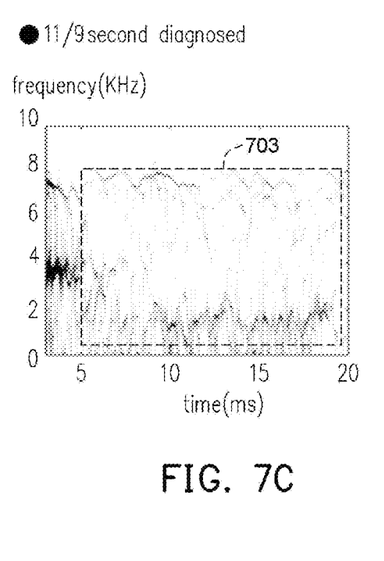

FIG. 7A, FIG. 7B, and FIG. 7C are soundprint images at different time points according to an embodiment of the invention. Referring to FIG. 7A, FIG. 7B, and FIG. 7C, for example, it is assumed that FIG. 7A illustrates the first soundprint image 1455(01) obtained by the user at the time of first time diagnosis on October 9 (first visit); FIG. 7B illustrates the first soundprint image 1455(02) obtained by the user at the time of second time diagnosis on October 26 (second visit); and FIG. 7C illustrates the first soundprint image 1455(03) obtained by the user at the time of the third time diagnosis on November 9 (third visit).

The hearing diagnosis management module 11 calculates a plurality of first soundprint densities corresponding to the first soundprint images 1455(01) to 1455(03) respectively according to images of specific regions 701, 702, and 703 of the first soundprint images (for example, calculating the pixel density of the gray corrugated image in the specific region). Then, the hearing diagnosis management module 11 calculates a difference between the soundprint densities of two soundprint images that are adjacent to each other in time. For example, the hearing diagnosis management module 11 calculates a difference (first soundprint density difference) by subtracting the soundprint density of the specific region 701 from the soundprint density of the specific region 702, and calculates another difference (second soundprint density difference) by subtracting the soundprint density of the specific region 702 from the soundprint density of the specific region 703. Whether the hearing of the tested ear is gradually recovering is determined according to the differences (the hearing recovery information is determined) (For example, if the second soundprint density difference is larger than the first soundprint density difference, it may indicate that the hearing of the tested ear is gradually recovering). To be more specific, a lower soundprint density of the specific region of the soundprint image indicates that the soundprint of the soundprint image is less obvious (clear), which means that the degree of hearing of the tested ear corresponding to the soundprint image is worse. On the other hand, a higher soundprint density of the specific region of the soundprint image indicates that the degree of hearing of the tested ear corresponding to the soundprint image is better (refer to the soundprint image of the ear having normal hearing shown in FIG. 5B).

That is, by calculating the differences between the soundprint densities of the soundprint images, the variation of the degree of hearing of the same ear under test may be determined. If the soundprint densities is increasing with time, it indicates that the degree of hearing of the tested ear is improving (that is, the hearing is gradually recovering). In contrast, if the soundprint densities of the soundprint images corresponding to the same ear under test do not show any increase with time, it is determined that the degree of hearing of the tested ear is not improving.

In an embodiment, if the difference between the soundprint densities that vary with time is greater than a threshold value, it is determined that the tested ear is recoverable, the tested ear is recovering, or the tested ear is expected to recover gradually. Next, the hearing diagnosis management module 11 uses the result of the determination described above as the hearing recovery information and adds it to the first hearing information. In the example shown in FIG. 7A to FIG. 7C, the hearing diagnosis management module 11 determines that the degree of hearing of the tested ear 146(3) is gradually recovering or recoverable. The hearing diagnosis management module 11 adds this result to the health information or the medical history information of the first hearing information (the third hearing information 1425(03)).

In another embodiment, the hearing diagnosis management module 11 may compare the first soundprint image 1455(03) with the soundprint images of other ears under test to find the most similar ones (e.g., the similarity calculated according to the first soundprint image 1455(03) the most similar soundprint image exceeds a soundprint similarity threshold value) through image comparison, and generate the first hearing information according to the hearing information corresponding to the most similar soundprint image, or determine the hearing recovery information of the tested ear 146(3) according to the hearing recovery information in the hearing information corresponding to the most similar soundprint image.

It should be noted that, in this embodiment, the otoacoustic emission detecting module 12 may also perform calibration with respect to the shape of the outer ear canal of the subject under test, the acoustic characteristics of the sound receiving device and the sound source device, so as to further improve the accuracy of the obtained otoacoustic emission waveform. Moreover, the otoacoustic emission detecting module 12 may perform another otoacoustic emission detecting operation to the ear in pair with the tested ear, so as to help calibrate/correct the health information obtained from the first hearing diagnosis image.

The foregoing modules/units may be respectively implemented by specific hardware circuits performing corresponding function(s)/operation(s), but the invention is not limited thereto. For example, the foregoing modules/units may be respectively implemented by specific program codes/procedures/applications stored in the storage unit (circuit) and accessed by a processing unit (e.g., processor) of the hearing diagnosis device to perform corresponding function(s)/operation(s). Furthermore, the above-described method according to the present invention can be implemented in either hardware (e.g., circuit), firmware, or software (e.g., program codes/procedures/applications) that can be stored in a recording medium such as a CD ROM, RAM, floppy disk, hard disk or magneto-optical disk, Software, or computer code stored on a non-transient machine-readable medium such that the methods described herein may be implemented in software that uses a general purpose computer or a specialized processor or a programmable or specialized hardware such as an ASIC Or FPGA). It should be understood by those of ordinary skill in the art that a computer, processor, microprocessor controller, or programmable hardware includes storage elements (e.g., RAM, ROM, flash memory, etc.) that can store or receive software), The processor or hardware implements the processing methods described herein when the software is accessed and executed by a computer. In addition, it should be noted that, when the general computer accesses the code for implementing the processing described herein, execution of the code transforms the general purpose computer into a dedicated computer for executing the processing described herein.

To sum up, the hearing diagnosis device and the hearing diagnosis method of the invention perform the otoacoustic emission detecting operation on the ear of the subject under test, so as to obtain the hearing diagnosis image. Then, through comparison between the hearing diagnosis image and the hearing diagnosis image sample database, the health condition (hearing information) of the ear of the subject under test is determined correspondingly. In addition, according to the hearing diagnosis device and the hearing diagnosis method of the invention, the hearing recovery probability (e.g., the probability of recovery of hearing after treatment or the probability of recovery of hearing that is currently damaged) of the subject under test (patient) may be predicted specifically. The soundprint images may also be used for observing variation of the soundprint images of different diagnosis with time, so as to determine the healing progress of the patient. Thus, the medical personnel or relevant medical personnel may have quantitative data (foregoing databases) as reference for designing a course of treatment for the patient's hearing (the hearing of the subject under test).

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:
1. A hearing diagnosis device, comprising:
a storage circuit configured to store a hearing diagnosis image sample database and a hearing information sample database, wherein the hearing diagnosis image sample database records a plurality of hearing diagnosis image samples and the hearing information sample database records a plurality of hearing information samples respectively corresponding to the hearing diagnosis image samples, wherein each of the hearing information samples comprises health information, identity information, and medical history information of a tested ear of the corresponding hearing diagnosis image sample;
an otoacoustic emission detecting circuit; and
a processor, coupled to the storage circuit and the otoacoustic emission detecting circuit, wherein the processor executes program code to implement a hearing diagnosis method, wherein
the processor is configured to respectively generate a plurality of hearing models according to a plurality of parameter sets,
wherein each of the hearing models is a cochlea biophysical model for describing a wave propagation of a vibrating sound of a human cochlea, wherein the vibrating sound is generated by the cochlea in response to a test audio, wherein an electric model of outer hair cells of the cochlea is embedded in each of the hearing models,
wherein each of the parameter sets comprises a plurality of parameters corresponding to different parts of a human ear and a health function corresponding to the human ear, wherein the parameters of each of the parameter sets comprise material properties of the Organ of Corti from high frequency to low frequency and cross-sectional areas of each part of the cochlea,
the processor is further configured to respectively input the test audio to the generated hearing models to generate a plurality of simulated hearing diagnosis images respectively corresponding to the hearing models, and use the parameter sets to generate a plurality of simulated hearing information respectively corresponding to the simulated hearing diagnosis images,
wherein the otoacoustic emission detecting circuit is configured to perform an otoacoustic emission detecting operation by playing the test audio to an ear of a user to obtain a first hearing diagnosis image corresponding to the ear,
the processor is further configured to execute a hearing diagnosis operation corresponding to the first hearing diagnosis image according to the first hearing diagnosis image, the hearing diagnosis image samples, and the hearing information samples by comparing the first hearing diagnosis image with the hearing diagnosis image samples, so as to determine first hearing information of the ear,
wherein the hearing diagnosis image samples comprise a plurality of simulated hearing diagnosis image samples, and the hearing information samples comprise a plurality of simulated hearing information samples, wherein the first hearing diagnosis image and each of the hearing diagnosis image samples respectively record an otoacoustic emission (OAE) waveform,
wherein the storage circuit further stores a soundprint image history record database that records a first soundprint image history record corresponding to the user, wherein the first soundprint image history record comprises one or more first soundprint images, which are stored at different time points respectively, corresponding to the user,
wherein in the otoacoustic emission detecting operation, the otoacoustic emission detecting circuit is further configured to generate a first soundprint image according to the OAE waveform of the first hearing diagnosis image, and store the first soundprint image to the first soundprint image history record, wherein a horizontal axis coordinate of the first soundprint image represents a time and a vertical axis coordinate of the first soundprint image represents a frequency,
wherein in the hearing diagnosis operation corresponding to the first hearing diagnosis image,
the processor is further configured to calculate a plurality of first soundprint densities corresponding to different time points according to an image of a specific region of the first soundprint image corresponding to the different time points in the first soundprint image history record, wherein a horizon- tal axis range of the specific region is 1-20 ms and a vertical axis range of the specific region is 1-10 kHz, the processor is further configured to determine first hearing recovery information of the user according to a variation of the first soundprint densities corresponding to the different time points, and the processor is further configured to add the first hearing recovery information into the first hearing information of the ear.

2. The hearing diagnosis device according to claim 1, wherein in the hearing diagnosis operation corresponding to the first hearing diagnosis image, the processor calculates a similarity between the first hearing diagnosis image and each of the hearing diagnosis image samples to obtain a plurality of similarities, and the processor determines whether a matched hearing diagnosis image corresponding to the first hearing diagnosis image exists among the hearing diagnosis image samples according to the calculated similarities and a similarity threshold value, and wherein if a first similarity, which is maximum among the similarities, exceeds the similarity threshold value, the processor determines that a first hearing diagnosis image sample corresponding to the first similarity is the matched hearing diagnosis image corresponding to the first hearing diagnosis image among the hearing diagnosis image samples, and uses a first hearing information sample corresponding to the first hearing diagnosis image sample determined as the matched hearing diagnosis image as the first hearing information of the ear of the user.

3. The hearing diagnosis device according to claim 1, wherein the processor stores the simulated hearing diagnosis image samples to the hearing diagnosis image sample database, and wherein the processor stores the simulated hearing information samples to the hearing information sample database.

4. The hearing diagnosis device according to claim 3, wherein in the hearing diagnosis operation corresponding to the first hearing diagnosis image, the processor executes one or more iterative operations according to the first hearing diagnosis image to obtain a clinical hearing model and a clinical parameter set corresponding to the clinical hearing model, wherein the processor generates the first hearing information of the ear of the user according to the clinical parameter set.

5. The hearing diagnosis device according to claim 4, wherein the operation of the processor executing the one or more iterative operations according to the first hearing diagnosis image to obtain the clinical hearing model and the clinical parameter set corresponding to the clinical hearing model comprises:

(1) when executing one iterative operation, the processor generates an iterative hearing model according to an iterative parameter set corresponding to the one iterative operation, and inputs the test audio to the generated iterative hearing model to obtain an iterative hearing diagnosis image;

(2) the processor calculates a deviation value between the iterative hearing diagnosis image and the first hearing diagnosis image;

(3) if the deviation value is not smaller than a deviation value threshold value, the processor correspondingly adjusts the iterative parameter set according to the deviation value and takes the adjusted iterative parameter set as an iterative parameter set corresponding to a next iterative operation, and re-executes the operation (1) to perform the next iterative operation; and (4) if the deviation value is smaller than the deviation value threshold value, the processor takes the iterative hearing model as the clinical hearing model and takes the iterative parameter set as the clinical parameter set.

6. The hearing diagnosis device according to claim 2, wherein the hearing diagnosis image samples comprise a plurality of clinical hearing diagnosis image samples divided into a clinical sample group, and the hearing information samples comprise a plurality of clinical hearing information samples that are divided into the clinical sample group and respectively correspond to the clinical hearing diagnosis image samples, wherein in response to completion of determining the first hearing information of the ear, the processor takes the first hearing diagnosis image as a clinical hearing diagnosis image sample and stores the clinical hearing diagnosis image sample to the clinical sample group, and stores the determined first hearing information as a corresponding clinical hearing information sample to the clinical sample group.

7. The hearing diagnosis device according to claim 1, wherein the OAE waveform of the first hearing diagnosis image represents a sound pressure of a responsive vibrating sound that the ear generates with time in response to the test audio played to the ear.

8. The hearing diagnosis device according to claim 7, wherein the first hearing recovery information comprises a recovery prediction, a recovery progress, a recovery probability of hearing of the ear, or a combination thereof.

9. A hearing diagnosis method, adapted to a hearing diagnosis device, wherein the hearing diagnosis device comprises a storage circuit, an otoacoustic emission detecting circuit, and a processor, comprising:

generating, by the processor, a plurality of hearing models respectively according to a plurality of parameter sets, wherein each of the hearing models is a cochlea biophysical model for describing a wave propagation of a vibrating sound of a human cochlea, wherein the vibrating sound is generated by the cochlea in response to a test audio, wherein an electric model of outer hair cells of the cochlea is embedded in each of the hearing models, wherein each of the parameter sets comprises a plurality of parameters corresponding to different pails of a human ear and a health function corresponding to the human ear, wherein the parameters of each of the parameter sets comprise material properties of the Organ of Corti from high frequency to low frequency and cross-sectional areas of each part of the cochlea;

inputting, by the processor, the test audio respectively to the generated hearing models to generate a plurality of simulated hearing diagnosis images respectively corresponding to the hearing models, and using the parameter sets to generate a plurality of simulated hearing information respectively corresponding to the simulated hearing diagnosis images, performing, by the otoacoustic emission detecting circuit, an otoacoustic emission detecting operation by playing the test audio to an ear of a user to obtain a first hearing diagnosis image corresponding to the ear; and executing, by the processor, a hearing diagnosis operation corresponding to the first hearing diagnosis image according to the first hearing diagnosis image, a plurality of hearing diagnosis image samples, and a plurality of hearing information samples respectively corresponding to the hearing diagnosis image samples by comparing the first hearing diagnosis image with the hearing diagnosis image samples, so as to determine first hearing information of the ear, wherein the hearing diagnosis image samples comprise a plurality of simulated hearing diagnosis image samples, and the hearing information samples comprise a plurality of simulated hearing information samples, wherein the first hearing diagnosis image and each of the hearing diagnosis image samples respectively record an otoacoustic emission (OAE) waveform, wherein the storage circuit stores a soundprint image history record database that records a first soundprint image history record corresponding to the user, wherein the first soundprint image history record comprises one or more first soundprint images, which are stored at different time points respectively, corresponding to the user;

wherein the step of performing the otoacoustic emission detecting operation further comprises:
  generating, by the otoacoustic emission detecting circuit, a first soundprint image according to the OAE waveform of the first hearing diagnosis image, and storing, by the otoacoustic emission detecting circuit, the first soundprint image to the first soundprint image history record, wherein a horizontal axis coordinate of the first soundprint image represents a time and a vertical axis coordinate of the first soundprint image represents a frequency; and wherein the step of executing the hearing diagnosis operation corresponding to the first hearing diagnosis image comprises:
  calculating, by the processor, a plurality of first soundprint densities corresponding to different time points according to an image of a specific region of the first soundprint image corresponding to the different time points in the first soundprint image history record, wherein a horizontal axis range of the specific region is 1-20 ms and a vertical axis range of the specific region is 1-10 kHz,
  determining, by the processor, first hearing recovery information of the user according to a variation of the first soundprint densities corresponding to the different time points; and
  adding the first hearing recovery information into the first hearing information of the ear, wherein each of the hearing information samples comprises health information, identity information, and medical history information of a tested ear of the corresponding hearing diagnosis image sample.

10. The hearing diagnosis method according to claim 9, wherein executing the hearing diagnosis operation corresponding to the first hearing diagnosis image according to the first hearing diagnosis image, the hearing diagnosis image samples, and the hearing information samples respectively corresponding to the hearing diagnosis image samples to determine the first hearing information of the ear comprises:
  calculating a similarity between the first hearing diagnosis image and each of the hearing diagnosis image samples to obtain a plurality of similarities, and determining whether a matched hearing diagnosis image corresponding to the first hearing diagnosis image exists among the hearing diagnosis image samples according to the calculated similarities and a similarity threshold value; and
  if a first similarity which is maximum among the similarities exceeds the similarity threshold value, determining a first hearing diagnosis image sample corresponding to the first similarity as the matched hearing diagnosis image corresponding to the first hearing diagnosis image among the hearing diagnosis image samples, and taking a first hearing information sample corresponding to the first hearing diagnosis image sample determined as the matched hearing diagnosis image as the first hearing information of the ear of the user.

11. The hearing diagnosis method according to claim 9, further comprising:
  storing the simulated hearing diagnosis image samples to a hearing diagnosis image sample database; and
  storing the simulated hearing information samples to a hearing diagnosis information sample database.

12. The hearing diagnosis method according to claim 11, wherein executing the hearing diagnosis operation corresponding to the first hearing diagnosis image comprises:
  executing one or more iterative operations according to the first hearing diagnosis image to obtain a clinical hearing model and a clinical parameter set corresponding to the clinical hearing model; and
  generating the first hearing information of the ear of the user according to the clinical parameter set.

13. The hearing diagnosis method according to claim 12, wherein executing the one or more iterative operations according to the first hearing diagnosis image to obtain the clinical hearing model and the clinical parameter set corresponding to the clinical hearing model comprises:
  (1) when executing one iterative operation, generating an iterative hearing model according to an iterative parameter set corresponding to the one iterative operation, and inputting the test audio to the generated iterative hearing model to obtain an iterative hearing diagnosis image;
  (2) calculating a deviation value between the iterative hearing diagnosis image and the first hearing diagnosis image;
  (3) if the deviation value is not smaller than a deviation value threshold value, correspondingly adjusting the iterative parameter set according to the deviation value and taking the adjusted iterative parameter set as an iterative parameter set corresponding to a next iterative operation, and re-executing the operation (1) to perform the next iterative operation; and
  (4) if the deviation value is smaller than the deviation value threshold value, taking the iterative hearing model as the clinical hearing model and taking the iterative parameter set as the clinical parameter set.

14. The hearing diagnosis method according to claim 10, wherein the hearing diagnosis image samples comprise a plurality of clinical hearing diagnosis image samples divided into a clinical sample group, and the hearing information samples comprise a plurality of clinical hearing information samples that are divided into the clinical sample group and respectively correspond to the clinical hearing diagnosis image samples, and the hearing diagnosis method further comprises:
  in response to completion of determining the first hearing information of the ear, taking the first hearing diagnosis image as a clinical hearing diagnosis image sample and storing the clinical hearing diagnosis image sample to the clinical sample group, and storing the determined first hearing information as a corresponding clinical hearing information sample to the clinical sample group.

15. The hearing diagnosis method according to claim 9, wherein the OAE waveform of the first hearing diagnosis image represents a sound pressure of a responsive vibrating sound that the ear generates with time in response to the test audio played to the ear.

16. The hearing diagnosis method according to claim 15, wherein the first hearing recovery information comprises a recovery prediction, a recovery progress, a recovery probability of hearing of the ear, or a combination thereof.

\* \* \* \* \*